US012564523B2

(12) United States Patent
Yoshiba

(10) Patent No.: US 12,564,523 B2
(45) Date of Patent: Mar. 3, 2026

(54) INDIVIDUALLY WRAPPED ABSORBENT ARTICLE AND METHOD FOR MANUFACTURING INDIVIDUALLY WRAPPED ABSORBENT ARTICLE

(71) Applicant: DAIO PAPER CORPORATION, Ehime (JP)

(72) Inventor: Megumi Yoshiba, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 788 days.

(21) Appl. No.: 17/758,162

(22) PCT Filed: Jun. 22, 2021

(86) PCT No.: PCT/JP2021/023631
§ 371 (c)(1),
(2) Date: Jun. 29, 2022

(87) PCT Pub. No.: WO2022/024591
PCT Pub. Date: Feb. 3, 2022

(65) Prior Publication Data
US 2023/0060828 A1     Mar. 2, 2023

(30) Foreign Application Priority Data

Jul. 28, 2020    (JP) ................................. 2020-127324

(51) Int. Cl.
*A61F 13/551* (2006.01)
*A61F 13/15* (2006.01)
(52) U.S. Cl.
CPC .... *A61F 13/5514* (2013.01); *A61F 13/15739* (2013.01); *A61F 13/15764* (2013.01)

(58) Field of Classification Search
CPC ............ A61F 13/5514; A61F 13/15739; A61F 13/15764; A61F 13/15747; B29C 2059/023; B29C 59/04; B29C 59/026
See application file for complete search history.

(56) References Cited

U.S. PATENT DOCUMENTS 5,181,610 A     1/1993  Quick et al.
10,143,603 B2 * 12/2018  Nomoto ............ A61F 13/15747
(Continued)

FOREIGN PATENT DOCUMENTS

CA          2785189        7/2011
JP       2006-340978      12/2006
(Continued)

OTHER PUBLICATIONS

JP 2020005666 A Description Translation (Year: 2018).*
(Continued)

*Primary Examiner* — Catharine L Anderson
*Assistant Examiner* — Hans Kaliher
(74) *Attorney, Agent, or Firm* — IPUSA, PLLC

(57)          ABSTRACT
An individually wrapped absorbent article that includes an absorbent article, and a wrapping sheet configured to wrap the absorbent article is provided. The wrapping sheet is folded toward an inner surface of the wrapping sheet so as to cause a first region including one end in a first direction of the wrapping sheet and a second region including an opposite end in the first direction to overlap with each other, and a seal portion is formed at each edge portion in a second direction of the wrapping sheet. The second direction is perpendicular to the first direction. The seal portion includes a plurality of compressed recesses and compressed projections along the first direction. The compressed projections are formed between the compressed recesses.

9 Claims, 7 Drawing Sheets

100

(56)                        References Cited

U.S. PATENT DOCUMENTS

| 2007/0049891 A1 * | 3/2007 | Clark, Jr. ............ A61F 13/5513 |
| | | 604/385.13 |
| 2009/0105680 A1 * | 4/2009 | Amiot ................. A61F 13/5514 |
| | | 604/385.13 |
| 2010/0057031 A1 | 3/2010 | Kuroda et al. |
| 2011/0306945 A1 | 12/2011 | Drevik et al. |
| 2012/0048769 A1 * | 3/2012 | Sivik ........................ A61Q 5/00 |
| | | 206/524.1 |

FOREIGN PATENT DOCUMENTS

| JP | 2007-167416 | 7/2007 | | |
| JP | 2008-080046 | 4/2008 | | |
| JP | 2011-140344 | 7/2011 | | |
| JP | 2012-511993 | 5/2012 | | |
| JP | 2014-195540 | 10/2014 | | |
| JP | 2019-084142 | 6/2019 | | |
| JP | 2020-005666 | 1/2020 | | |
| JP | 2020005666 A * | 1/2020 | ............. A61F 13/84 |
| WO | 2008/062873 | 5/2008 | | |
| WO | 2013/031647 | 3/2013 | | |

OTHER PUBLICATIONS

Extended European Search Report for 21850236.7 mailed on Dec. 13, 2023.
International Search Report for PCT/JP2021/023631 filed on Sep. 14, 2021.

* cited by examiner (a)                    (b)

(c)                    (d)

(a)

(b)

1

INDIVIDUALLY WRAPPED ABSORBENT ARTICLE AND METHOD FOR MANUFACTURING INDIVIDUALLY WRAPPED ABSORBENT ARTICLE

TECHNICAL FIELD

The present invention relates to an individually wrapped absorbent article and a method for manufacturing the individually wrapped absorbent article.

BACKGROUND ART

Absorbent articles such as sanitary napkins, panty liners, and incontinence pads are often provided in an individually wrapped form. Typical examples of such an absorbent article provided in an individually wrapped form (an individually wrapped absorbent article) include an individually wrapped absorbent article in which an absorbent article is wrapped by folding a wrapping sheet together with the absorbent article in the lengthwise direction of the wrapping sheet, and both edge portions in the widthwise direction of the wrapping sheet are removably sealed.

For example, Patent Document 1 discloses an individual package in which an absorbent article is wrapped by folding a wrapping sheet along one or more folding lines, and seal regions of the wrapping sheet are sealed in a direction parallel to the folding lines. The seal regions are formed at both edge portions in a direction parallel to the folding lines of the wrapping sheet, and a plurality of seal units are intermittently provided in the seal regions. In the individual package disclosed in Patent Document 1, adhesion portions in the seal regions of the wrapping sheet are fused.

RELATED-ART DOCUMENTS

Patent Documents

Patent Document 1: Japanese Laid-open Patent Publication No. 2019-84142

SUMMARY OF THE INVENTION

Problem to be Solved by the Invention

In recent years, a wrapping sheet formed of a refractory material or a wrapping sheet having a layer of a refractory material on the surface of the wrapping sheet have been considered. If such a material is used for a wrapping sheet, it may be difficult to sufficiently bond layers of the wrapping sheet by heat fusion. Thus, the edge portions of the wrapping sheet cannot often have sufficient seal strength.

In view of the above, it is an object of one aspect of the present invention to provide an individually wrapped absorbent article in which a seal portion has sufficient seal strength and a wrapping sheet can be formed of any of various materials.

Means to Solve the Problem

According to an embodiment of the present invention, an individually wrapped absorbent article that includes an absorbent article, and a wrapping sheet configured to wrap the absorbent article is provided. The wrapping sheet is folded toward an inner surface of the wrapping sheet so as to cause a first region including one end in a first direction of the wrapping sheet and a second region including an opposite end in the first direction to overlap with each other, and a seal portion is formed at each edge portion in a second direction of the wrapping sheet. The second direction is perpendicular to the first direction. The seal portion includes a plurality of compressed recesses and compressed projections along the first direction. The compressed projections are formed between the compressed recesses.

Effects of the Invention

According to one aspect of the present invention, an individually wrapped absorbent article, in which a seal portion has sufficient seal strength and a wrapping sheet can be formed of any of various materials, can be provided.

MODE FOR CARRYING OUT THE INVENTION

Figure 1:
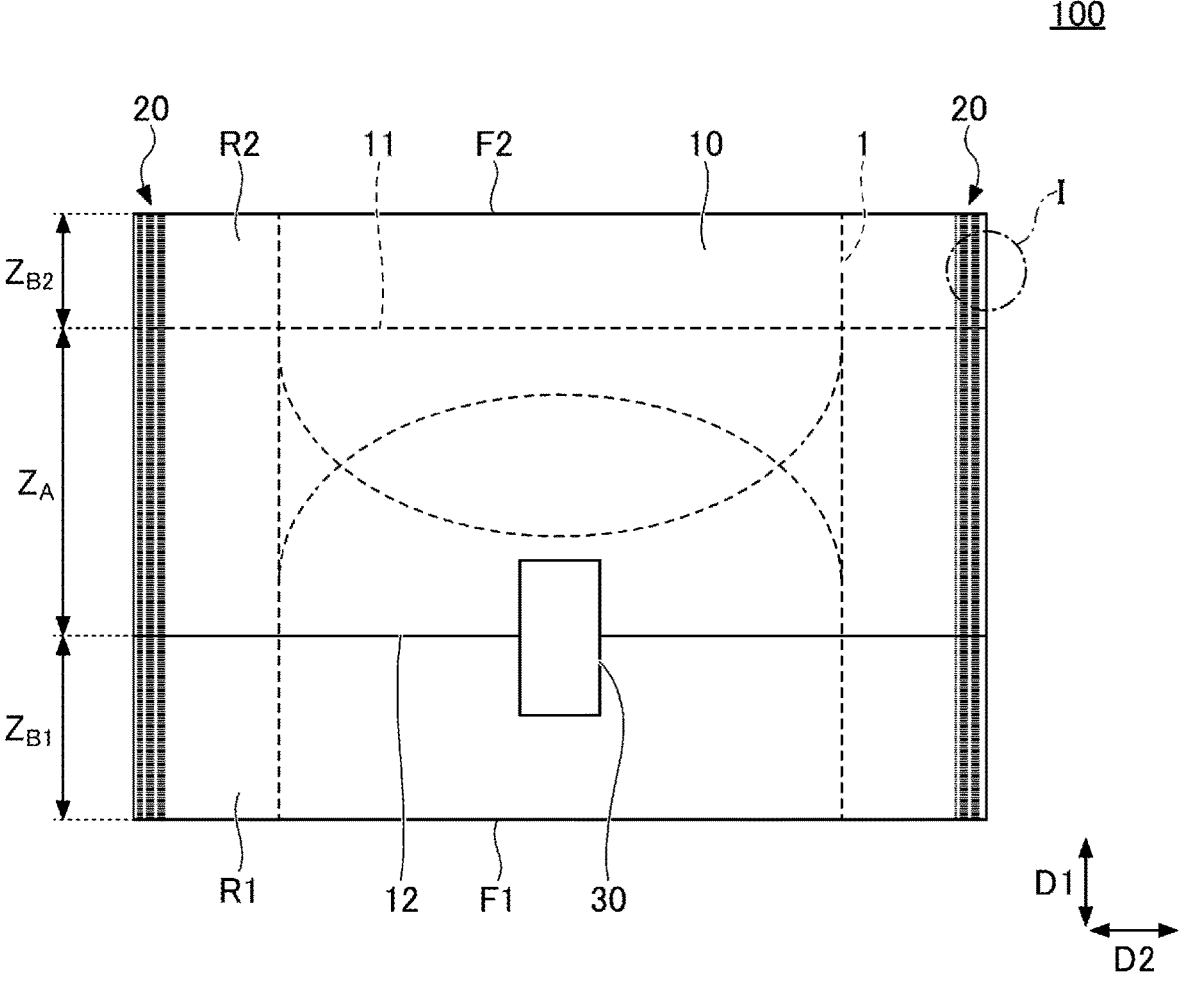
FIG. 1 is a plan view of an individually wrapped absorbent article that includes a wrapping sheet and an absorbent article according to an embodiment of the present invention.

In the following, embodiments of the present invention will be described with reference to the accompanying drawings. In the drawings, unless otherwise noted, elements having the same or corresponding configurations are designated by the same reference numerals and the description thereof may be omitted. Further, in order to facilitate understanding of the present invention, the drawings are schematically illustrated.

Figure 2:
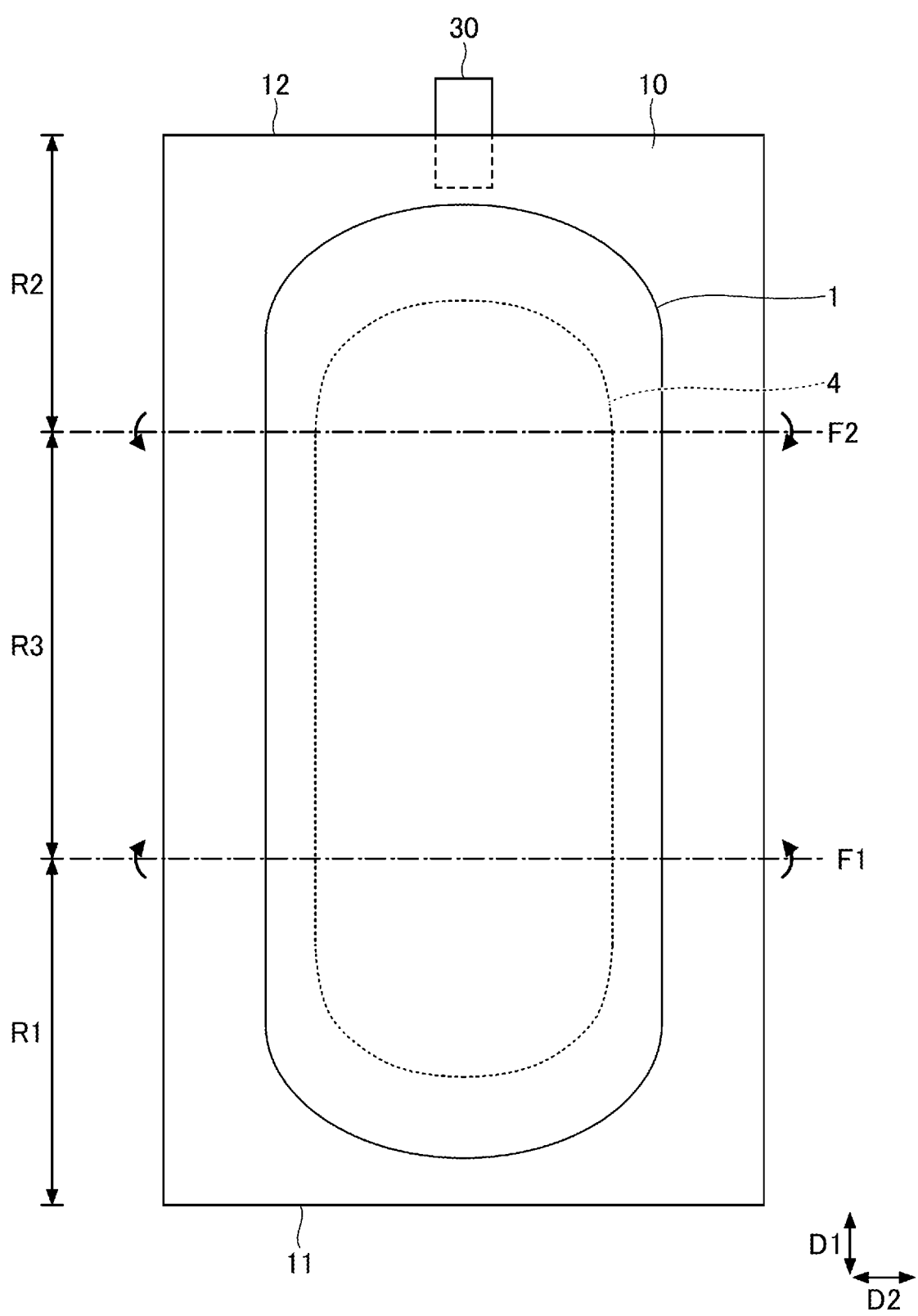
FIG. 2 is a plan view of an unfolded state of the wrapping sheet of the individually wrapped absorbent article as viewed from the side of the wrapping sheet on which the absorbent article is placed.

FIG. 1 is a plan view of an individually wrapped absorbent article 100 that includes a wrapping sheet 10 and an absorbent article 1 according to an embodiment of the present invention. The absorbent article 1 to be wrapped according to the present embodiment may be a flat absorbent article such as a sanitary napkin, a panty liner, an incontinence pad, or the like. Further, FIG. 2 illustrates an unfolded state of the individually wrapped absorbent article 100 of FIG. 1, or illustrates the absorbent article 1 that is placed on the wrapping sheet 10 and is yet to be wrapped.

(Absorbent Article)

The absorbent article 1 included in the individually wrapped absorbent article 100 according to the present embodiment has an elongated shape in a plan view; however, the shape of the absorbent article 1 in a plan view is not limited the elongated shape as illustrated in the drawings. For example, the absorbent article 1 may have a regular polygonal shape including a square shape, a circular shape, or the like in a plan view. Further, the absorbent article 1 may have any shape and any size such that the absorbent article 1 can be wrapped in a wrapping sheet without being folded together with the wrapping sheet. If the absorbent article 1 has an elongated shape as illustrated in FIG. 1 and FIG. 2, the entire length (the length in the lengthwise direction) of the absorbent article 1 can be 140 mm to 420 mm, and the width (the length in the widthwise direction) of the absorbent article 1 can be 50 mm to 110 mm.

The absorbent article 1 may have a structure in which a liquid-impermeable back sheet, an absorbent body, and a liquid-permeable top sheet are laminated in this order. As the back sheet, a sheet material having at least a water shielding property, such as an olefin resin sheet formed of ethylene or polypropylene, may be used. In addition, a laminated non-woven fabric formed by laminating a non-woven material onto a polyethylene sheet or the like, or a non-woven fabric laminated sheet that is substantially liquid-impermeable by interposing a waterproof film may be used. Further, a material having moisture permeability may be used.

As the top sheet, a porous or non-porous non-woven fabric, a porous plastic sheet, or the like may be preferably used. Examples of material fibers constituting the non-woven fabric include olefins such as polyethylene and polypropylene; synthetic fibers such as polyester and polyamide; regenerated fibers such as rayon and cuprammonium rayon; mixed fibers thereof; and natural fibers such as cotton. These fibers can be used alone or in combination with two or more kinds.

An absorbent body 4 has a size and a shape so as not to extend beyond the top sheet and the back sheet. The outer edges of the back sheet and the top sheet, located forward of and rearward of the absorbent body, are bonded to each other with an adhesive such as a hot-melt adhesive or with an adhesive means such as a heat seal or an ultrasonic seal.

The material of the absorbent body 4 is not particularly limited as long as the absorbent body 4 can absorb and retain body fluids, and preferably includes cotton-like pulp and a water-absorptive polymer. Examples of the water-absorptive polymer include a superabsorbent polymer (SAP), a superabsorbent polymer fiber (SAF), and a combination thereof. Examples of the pulp include cellulose fibers such as dissolving pulp and chemical pulp made from wood, and synthetic cellulose fibers such as rayon and acetate.

The thickness of the absorbent body 4 may be in the range of 0.5 mm to 25 mm, and preferably in the range of 1.5 mm to 6.5 mm. The absorbent body may have a structure in which a region of the absorbent body 4 corresponding to a body fluid excretion orifice (a body fluid excretion orifice corresponding region) may be inflated, or a region of the absorbent body 4 facing a groove of the buttocks and located rearward of the body fluid excretion orifice corresponding region may be inflated.

Further, side non-woven fabrics, extending along the lengthwise direction, may be provided on both sides of the absorbent article 1. As the side nonwoven fabrics, water-repellent nonwoven fabrics or hydrophilic non-woven fabrics may be used.

(Structure of Individually Wrapped Absorbent Article)

As illustrated in FIG. 1 and FIG. 2, in the individually wrapped absorbent article 100, the single absorbent article 1 may be wrapped in the single wrapping sheet 10. The shape of the wrapping 2C sheet 10 is not particularly limited. However, in an unfolded state as illustrated in FIG. 2, the wrapping sheet 10 preferably has an elongated shape, such as a rectangular shape or an elongated oval shape. The absorbent article 1 can be hygienically wrapped by placing the absorbent article 1 having, for example, a flat and elongated shape on the wrapping sheet 10 and folding the absorbent article 1 and the wrapping sheet 10 together. In this specification, the surface of the wrapping sheet 10 on which the absorbent article 1 is placed is referred to as an inner surface. In addition, the surface on the opposite side of the wrapping sheet 10 from the inner surface, that is, the surface of the wrapping sheet 10 exposed to the outside of the individually wrapped absorbent article 100 is referred to as an outer surface.

A method for folding the wrapping sheet 10 is not particularly limited, as long as the wrapping sheet 10 is folded along one or more folding lines and can wrap the absorbent article 1 such that the absorbent article 1 is not exposed to the outside. FIG. 2 illustrates an example in which the wrapping sheet 10 is tri-folded (folded inward). As illustrated in FIG. 2, the wrapping sheet 10 includes a first region R1 and a second region R2. The first region R1 includes one end 11 in the first direction D1 of the wrapping sheet 10, and the second region R2 include an opposite end 12 in the first direction D1 of the wrapping sheet 10. The wrapping sheet 10 wraps the absorbent article 1 such that the second region R2 overlaps with the outer surface of the first region R1. More specifically, first, the first region R1 is folded along a first folding line F1. The first folding line F1 extends in the second direction D2, perpendicular to the first direction D1, of the wrapping sheet 10. After the first region R1 is folded, the second region R2 is folded along a second folding line F2, which extends in the second direction D2, such that the second region R2 overlaps with the outer surface of the first region R1. In this manner, the absorbent article 1 is wrapped in the wrapping sheet 10 (FIG. 1). A method for overlapping the two regions at both ends in the first direction D1 of the wrapping sheet 10 as described above is easy and preferable. With this method, the absorbent article can be securely enclosed without being exposed to an external environment.

In the present embodiment, a region between the first region R1 and the second region R2 is referred to as a third region R3 (FIG. 2). Further, in the present embodiment, the first direction D1 is the lengthwise direction of the wrapping sheet 10, and is also the lengthwise direction of the absorbent article 1 wrapped by the wrapping sheet 10. The second direction D2 is the widthwise direction of the wrapping sheet 10, and is also the widthwise direction of the absorbent article 1 wrapped by the wrapping sheet 10.

It is preferable to adjust the length in the first direction D1 of the first region R1, such that the one end 11 in the first direction D1 (lengthwise direction) of the wrapping sheet 10 does not extend beyond the second folding line F2 when the first region R1 is folded along the first folding line F1. Further, when the second region R2 is folded along the second folding line F2, the second region R2 may be folded such that the opposite end 12 in the first direction D1 reaches the first folding line F1, or the second region R2 may be folded such that the opposite end 12 is spaced apart from the first folding line F1 and is located on the first region R1 as illustrated in FIG. 1.

After the first region R1 and the second region R2 are sequentially folded, a sealing tape 30 may be attached to the center in the second direction D2 (widthwise direction) of the wrapping sheet 10 so as to extend across the opposite end 12 of the wrapping sheet 10. That is, the sealing tape 30 may be attached so as to extend from the second region R2 to the first region R1. When a user opens the wrapped absorbent article, the user can peel the sealing tape 30 from the first region R1 and then pull the sealing tape 30 until the second region R2 is lifted together with the sealing tape 30. Then, by continuously pulling the sealing tape 30 toward the second folding line F2, the user can open the second region R2 in the first direction D1.

The size of the wrapping sheet 10 depends on the size and shape of the absorbent article 1 to be wrapped. For example, with the wrapping sheet 10 being unfolded, the length in the first direction D1 (lengthwise direction) of the wrapping sheet 10 can be 100 mm to 450 mm, and the length (width) in the second direction D2 (widthwise direction) of the wrapping sheet 10 can be 70 mm to 250 mm.

Note that the wrapping sheet 10 may be folded along one folding line. That is, the wrapping sheet 10 may be bi-folded. Alternatively, the wrapping sheet 10 may be folded along three or more folding lines. For example, in order to wrap a relative long absorbent article, a wrapping sheet 10 having a larger length may be used in accordance with the length of the absorbent article. In this case, the length of the first region R1, which is folded first, is set to be larger than the length of the third region R3. When the first region R1 is folded, first, a portion of the first region R1 is folded inward or outward along a third folding line. The third folding line is located between the first folding line F1 and the one end 11 and extends in the second direction D2. Then, the entire first region R1 is folded along the first folding line F1, and subsequently, the second region R2 is folded along the second folding line F2. In this manner, the wrapping sheet 10 can be quad-folded.

(Seal Portions)

After the wrapping sheet 10 is folded as described above, seal portions 20, 20 are formed at both edge portions in the second direction D2 of the wrapping sheet 10. In the individually wrapped absorbent article 100 according to the present embodiment, the edge portions of the wrapping sheet 10 refer to portions where the absorbent article 1 is not placed in a plan view. Preferably, the edge portions of the wrapping sheet 10 may be spaced inward from the edges in the second direction D2 by 10 mm to 40 mm.

Figure 3:
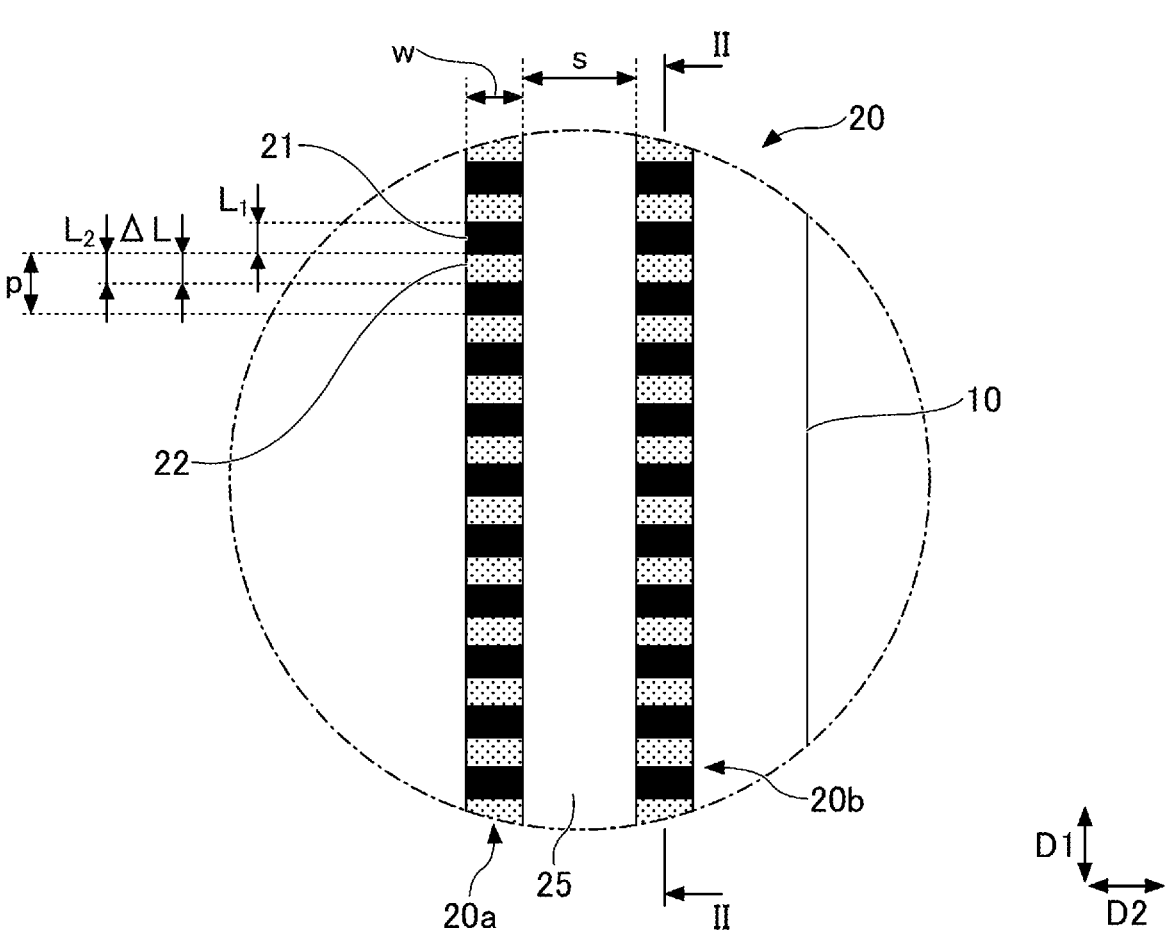
FIG. 3 is an enlarged view of a portion I of FIG. 1.
Figure 4:
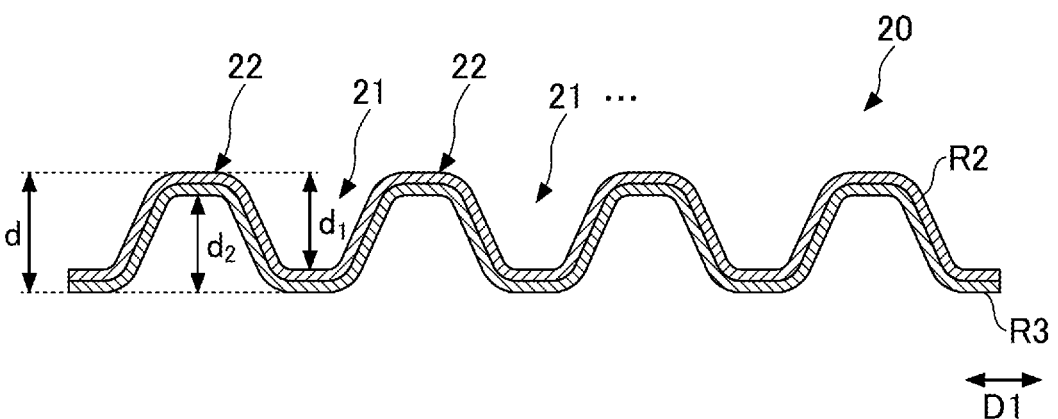
FIG. 4 is a partially enlarged view of a cross section taken through II-II of FIG. 3.

FIG. 3 is an enlarged view of a portion I of a seal portion 20 of FIG. 1. Further, FIG. 4 is a partially enlarged view of a cross section taken through II-II of FIG. 3. As illustrated in FIG. 3 and FIG. 4, the seal portion 20 includes a plurality of compressed recesses 21, 21, . . . and further includes compressed projections 22 between the compressed recesses 21, 21. In the present specification, a compressed recess 21 and a compressed projection 22 (which may be collectively referred to as a compressed portion) are portions that are compressed by applying pressure to the wrapping sheet 10 in the thickness direction and thus have a high material density. Further, a recess refers to a portion that is recessed from the surface position before the wrapping sheet is compressed toward one side (the bottom side, e.g., in the example of FIG. 1, the side on which the third region R3 is located) of the individually wrapped absorbent article 100 in the thickness direction, as viewed from the other side (the top side) of the individually wrapped absorbent article 100 (in the example of FIG. 1, the side on which the second region R2 is located). In addition, a projection refers to a portion that projects from the surface position before the wrapping sheet is compressed toward the above-described other side (the top side) of the individually wrapped absorbent article 100 in the thickness direction. In other words, a recess can refer to a portion that is recessed with respect to the surface of an uncompressed region of the wrapping sheet 10, which is located adjacent to the recess in the second direction D2. Similarly, the projection can refer to a portion that projects with respect to the surface of an uncompressed region of the wrapping sheet 10, which is located adjacent to the projection in the second direction D2. In the present embodiment, a recess as viewed from the top side of the individually wrapped absorbent article 100 can also be a projection as viewed from the bottom side. Similarly, a projection as viewed from the top side of the individually wrapped absorbent article 100 can also be a recess as viewed from the bottom side.

In the present embodiment, the seal portion 20 can be constituted by compressed portions, and portions of the wrapping sheet 10 do not need to be heat-fused or other materials (including an adhesive) do not need to be added. Accordingly, in the present embodiment, when the individually wrapped absorbent article 100 is manufactured, complicated work related to the seal portion 20, such as adjusting a temperature for heat fusion, can be avoided. However, the present embodiment does not necessarily exclude cases where the surface at the seal portion 20 of the wrapping sheet 10 is denatured or any other material is added to form a seal portion.

Further, as illustrated in FIG. 3 and FIG. 4, the compressed recess 21 and the compressed projection 22 are arranged adjacent to each other in the first direction D1. More specifically, the compressed recess 21 and the compressed projection 22 are alternately arranged in the first direction D1. Therefore, overlapping portions of the wrapping sheet 10 can be engaged and firmly fitted together, and high seal strength can be thus obtained. According to the present embodiment, high seal strength can be achieved by the physical structure of the seal portion 20. Therefore, even if a wrapping sheet formed of any of various materials, for example, a wrapping sheet that is unable to be heat-fused or difficult to be heat-fused, is used, a seal portion having sufficient seal strength can be formed. Accordingly, in the present embodiment, a material for the wrapping sheet 10 can be selected from a wider range of materials.

Accordingly, the compressed recess 21 and the compressed projection 22 in the present embodiment can be formed without portions of the wrapping sheet 10 being fused. With a configuration in which portions of the wrapping sheet 10 are not fused, a process for fusing the portions of the wrapping sheet is not required when the seal portion 20 is formed. Therefore, there is no need to perform a heating process and no need to adjust a temperature for heat fusion, thus avoiding complicated manufacturing work and reducing manufacturing costs. In other words, in the seal portion 20 according to the present embodiment, portions of the wrapping sheet 10 can be bonded to each other without being fused.

As illustrated in FIG. 3 and FIG. 4, the compressed recess 21 and the compressed projection 22 are continuously arranged in the first direction D1. That is, the seal portion 20 includes a strip-shaped portion or a linear-shape portion in which a compressed portion is continuous in the first direction D1. As illustrated in FIG. 3, in the present embodiment, the seal portion 20 includes seal lines 20a and 20b, and each of the seal lines 20a and 20b is constituted by a continuous compressed portion.

With the configuration in which the compressed recess 21 and the compressed projection 22 of the seal portion 20 are continuously arranged adjacent to each other along the first direction D1, overlapping portions of the wrapping sheet 10 can be stretched toward the top surface side and the bottom surface side of the individually wrapped absorbent article 100. Therefore, the compressed recess 21 can have a large depth and the compressed projection 22 can have a large height. In other words, in the seal portion 20, the compressed recess 21 have a large depth and the compressed projection 22 can have a large height with respect to a unit length in the first direction D1. Therefore, the overlapping portions of the wrapping sheet 10 can be more firmly engaged, and the seal strength of the seal portion 20 can be increased.

The depth $d_1$ (FIG. 4) of the compressed recess 21 may be preferably 0.1 mm to 1 mm, and more preferably 0.2 mm to 0.7 mm. Similarly, the height $d_2$ (FIG. 4) of the compressed projection 22 may be preferably 0.1 mm to 1 mm, and more preferably 0.2 mm to 0.7 mm.

The length L1 in the first direction D1 of the compressed recess 21 may be preferably 0.5 mm to 5 mm, more preferably 0.5 mm to 2 mm, and even more preferably 1 mm to 2 mm. By including the length L1 in the first direction D1 of the compressed recess 21 within the above-described range, compressed portions can be formed such that the overlapping portions of the wrapping sheet 10 can be sufficiently engaged and high seal strength can be thus provided. In addition, the above-described range is preferable in terms of using a pair of pressing rolls to form the seal portion 20. Similarly, the length L2 of in the first direction D1 of the compressed projection 22 may be preferably 0.5 mm to 5 mm, more preferably 0.5 mm to 2 mm, and even more preferably 1 mm to 2 mm.

Further, the distance ΔL in the first direction D1 between two adjacent compressed recesses 21 may be preferably 1 mm to 7 mm, more preferably 1 mm to 2 mm, and even more preferably 1 mm to 1.5 mm. By including the distance ΔL in the first direction D1 between two adjacent compressed recesses 21 within the above-described range, compressed portions can be formed such that the overlapping portions of the wrapping sheet 10 can be sufficiently engaged and high seal strength can be thus provided. In addition, the above-described range is preferable in terms of using the pair of pressing rolls to form the seal portion 20. Further, in the example illustrated in FIG. 3, the distance ΔL in the first direction D1 between two adjacent compressed recesses 21 is substantially equal to the length $L_2$ in the first direction D1 of the compressed projection 22.

The pitch p of compressed recesses 21 may be preferably 1 mm to 10 mm, and more preferably 2 mm to 4 mm. As illustrated in FIG. 3, the pitch p can be the distance from the end portion, closer to the one end 11 (closer to the folding line F1) in the first direction D1, of a given compressed recess 21 to the end portion, closer to the one end 11 (closer to the folding line F1) in the first direction D1, of a compressed recess 21 that is adjacent to the given compressed recess 21 in the first direction D1. Further, the pitch p may be a distance from the center in the first direction D1 of a given compressed recess 21 to the center in the first direction D1 of a compressed recess 21 that is adjacent to the given compressed recess 21 in the first direction D1. By including the pitch p within the above-described range, compressed portions can be formed such that the overlapping portions of the wrapping sheet 10 can be sufficiently engaged and high seal strength can be thus provided. In addition, the, the pitch p within the above-described range is preferable in terms of using the pair of pressing rolls to form the seal portion 20.

The length w in the second direction D2 of the compressed recess 21 may be preferably 0.5 mm to 5 mm, more preferably 0.5 mm to 2 mm, and even more preferably 1 mm to 2 mm. By including the width w in the second direction D2 of the compressed recess 21 within the above-described range, compressed portions can be formed such that the overlapping portions of the wrapping sheet 10 can be sufficiently engaged and high seal strength can be thus provided. In addition, in the process of using the pair of pressing rolls to form the seal portion 20, the width w within the above-described range is also preferable.

In the example illustrated in FIG. 3, the compressed recess 21 has a square-like shape, specifically a rectangular shape in a plan view, and the compressed recess 21 is arranged such that two sides of the compressed recess 21 are parallel to the first direction D1. However, the arrangement of the compressed recess 21 is not limited to that illustrated in the drawings. The compressed recess 21 may be arranged such that two sides of the rectangular shape of the compressed recess 21 may be inclined at a predetermined angle with respect to the first direction D1. Further, the shape of the compressed recess 21 in a plan view is not limited to that illustrated in the drawings, and may be a square shape other than a rectangular shape, such as a diamond shape or a trapezoid shape, a polygonal shape other than a square shape, a circular shape, an elliptical shape, a heart shape, a droplet shape, or the like.

The compressed projection 22 may have the above-described size and shape, and may obtain the same effects as those obtained from the above-described size and shape. Further, one or more of or all of the length in the first direction D1, the distance in the first direction D1, the width in the second direction, and the pitch can be the same between compressed recesses 21 and compressed projections 22 of the seal portion 20.

The compressed recess 21 may be spaced apart from the compressed projection 22 in the first direction D1. That is, a non-compressed portion, where the overlapping portions of the wrapping sheet 10 are not compressed, may be formed between the compressed recess 21 and the compressed projection 22. In a case where the seal portion 20 is formed by using the pair of pressing rolls and the first direction D1 is parallel to the axial direction of the rolls, forming a non-compressed portion in the first direction D1 can increase the linear pressure, thereby allowing pressure to be concentrated on compressed areas (projections of pressing portions of the rolls). Thus, the seal strength of the seal portion 20 can be further increased.

Further, in the example illustrated in FIG. 3, the seal portion 20 includes the seal lines 20a and 20b along the first direction D1. Each of the seal lines 20a and 20b is constituted by a continuous compressed portion. The seal portion 20 can include a plurality of seal lines along the first direction D1. In addition, a non-compressed portion 25 can be formed between the seal lines. That is, the non-compressed portion 25 is formed between compressed portions (each including the compressed recess 21 and the compressed projection 22) in the second direction D2. Accordingly, as viewed in the second direction D2, the non-compressed portion 25 is formed between the seal lines 20a and 20b or between the compressed portions. Therefore, pressure can be concentrated on the compressed portions, and as a result, the seal strength of the seal portion 20 can be further increased. Note that the number of seal lines as described above may be 2 to 5.

Further, the distance s between the seal lines 20a and 20b may be preferably 1 mm to 2 mm, and more preferably 1 mm to 1.5 mm. By including the distance s between the seal lines within the above-described range, an effect of concentrating pressure on compressed areas can be enhanced, and as a result, the seal strength of the seal portion 20 can be further increased.

(Material of Wrapping Sheet)

A material used for the wrapping sheet 10 of the individually wrapped absorbent article 100 is not particularly limited, and may be paper, a non-woven fabric, or a resin film. In the present embodiment, a wrapping sheet formed of a refractory material or a wrapping sheet including a layer of a refractory material on its surface may be preferably used. As used herein, the refractory material is a material that does not cause portions of a wrapping sheet to be fused when heated (for example, when heated to 80° C. or more).

If the wrapping sheet 10 includes paper, the environmental load at the time of manufacturing and/or disposal of the wrapping sheet 10 or the individually wrapped absorbent article 100 can be reduced. Further, a natural texture can be provided. Preferably, the wrapping sheet 10 can be formed of paper, or can use a sheet formed of paper subjected to any processing. As used herein, the "paper" can refer to plant fibers or other fibers that are bonded together with an adhesive and formed in a flat sheet shape. In particular, the "paper" can refer to paper containing, as a main component, plant fibers (pulp), e.g., paper containing 50% or more of plant fibers and preferably containing 80% or more of plant fibers. Examples of types of pulp contained in paper include wood pulp, non-wood pulp, and waste paper pulp, which may be either mechanical pulp or chemical pulp. Further, additives may be added to paper. Specific examples of paper used for the wrapping sheet 10 include various types of paper, such as western paper, Japanese paper, coated paper, synthetic paper, and the like. Further, paper typically used for other purposes, such as newsprint paper, printing paper (including fine paper), writing paper, drawing paper, wrapping paper, thin paper, or other various types of paper can be used with or without being coated.

If paper is used as the material of the wrapping sheet 10, the paper may be subjected to processing after papermaking. Examples of the above-described processing include creping, embossing, calendering, water-repellent coating, slitting, plying, printing, and the like. By performing creping and embossing, both strength and flexibility can be improved. In addition, if the wrapping sheet 10 is subjected to water-repellent coating, for example, a water-repellent agent containing a silicone-based resin, a paraffin-based resin, a fluoropolymer, or the like may be applied to at least one of the outer surface (which is exposed to the outside in a state in which the absorbent article 1 is wrapped) and the inner surface of the wrapping sheet 10.

If paper is used as the material of the wrapping sheet 10, the basis weight of the wrapping sheet can be preferably less than or equal to 50 g/m², and more preferably less than or equal to 40 g/m². The lower limit of the basis weight of the wrapping sheet 10 is not particularly limited as long as the wrapping sheet 10 can properly function. The lower limit of the basis weight of the wrapping sheet 10 can be preferably greater than or equal to 20 g/m², and more preferably greater than or equal to 15 g/m². Further, if the wrapping sheet 10 is made of paper, the thickness of the wrapping sheet 10 can be preferably 40 μm to 200 μm, and more preferably 100 μm to 200 μm.

If the wrapping sheet 10 includes a non-woven fabric, a texture and soft feel can be improved. A meltblown non-woven fabric or a spun-bonded non-woven fabric can be preferably used. Alternatively, a laminate of a plurality of layers of these non-woven fabrics can be used. Further, fibers constituting the non-woven fabric may be polyolefin such as polypropylene or polyethylene, or polyamide such as polyester or nylon.

If the wrapping sheet 10 includes a resin film, polyolefin such as polypropylene or polyethylene, polyester, polyvinyl alcohol, or the like can be used as a resin. As a resin film, a stretched resin film is preferable. An air-impermeable film or an air-permeable film may be used. If a resin film is used, the outline of a print pattern can be made clear and good color development of a colorant can be provided, thus improving the design of the wrapping sheet 10.

The wrapping sheet 10 may be a single layer sheet in which one wrapping sheet 10 is composed of any of the above-described materials. The wrapping sheet 10 may be a laminated sheet formed by laminating a plurality layers composed of different materials.

The stiffness of the wrapping sheet 10 is preferably 100 mm or more, and more preferably 105 mm or more. The stiffness may be measured in accordance with the 45° cantilever method specified in JIS L1096:2010, 8.21. By using the wrapping sheet 10 having the above-described stiffness, the stiffness of the seal portion 20 can also be increased. Therefore, it is possible to prevent a reduction in the seal strength of the seal portion 20 due to friction or the like of the wrapping sheet 10 when the wrapping sheet 10 is, for example, carried.

Modification

In the wrapping form described with reference to FIG. 1 and FIG. 2, the individually wrapped absorbent article 100 includes zones in which the number of overlapping portions of the wrapping sheet 10 differs as viewed in the first direction D1. More specifically, as illustrated in FIG. 1, the individually wrapped absorbent article 100 includes a first thin zone $Z_{B1}$, a second thin zone $Z_{B2}$, and a thick zone $Z_A$. In the first thin zone $Z_{B1}$, the third region R3 and the first region R1 of the wrapping sheet 10 are overlapped in this order, that is, two layers of the wrapping sheet 10 are overlapped. In the second thin zone $Z_{B1}$, the third region R3 and the second region R2 of the wrapping sheet 10 are overlapped in this order, that is, two layers of the wrapping sheet 10 are overlapped. In the thick zone $Z_A$, the third region R3, the first region R1, and the second region R2 are overlapped in this order.

As described above, when the number of overlapping portions of the wrapping sheet differs, the seal strength of the seal portion tends to be different. More specifically, as the number of overlapping portions of the wrapping sheet increases, compressed portions are compressed at higher pressure, and as a result, the seal strength tends to be increased. If the seal strength is excessively high, the individually wrapped absorbent article 100 would not be smoothly opened. Conversely, if the seal strength of the entire seal portion is reduced, the individually wrapped absorbent article 100 would be unintentionally opened in a zone where the number of overlapping portions of the wrapping sheet 10 is small. Accordingly, it is preferable to adjust the seal strength of the seal portion 20 in accordance with the number of overlapping portions of the wrapping sheet 10. That is, the seal strength of the seal portion 20 can be reduced in a zone where the number of overlapping portions of the wrapping sheet 10 is relatively large, and the seal strength of the seal portion 20 can be increased in a zone where the number of overlapping portions of the wrapping sheet 10 is relatively small.

Example configurations in which the seal strength of the seal portion 20 is reduced include a configuration in which the thickness of the seal portion 20 is reduced. The thickness of the seal portion 20 is not the thickness of overlapping portions of the wrapping sheet 10. The thickness of the seal portion 20 refers to the length d (FIG. 4) from the lowest position to the highest position of the seal portion 20. The seal portion 20 having a large thickness means that the compressed recess 21 has a large depth and the compressed projection 22 has a large height. Accordingly, portions of the wrapping sheet 10 can be more firmly engaged, and the seal strength can be increased.

Figure 5:
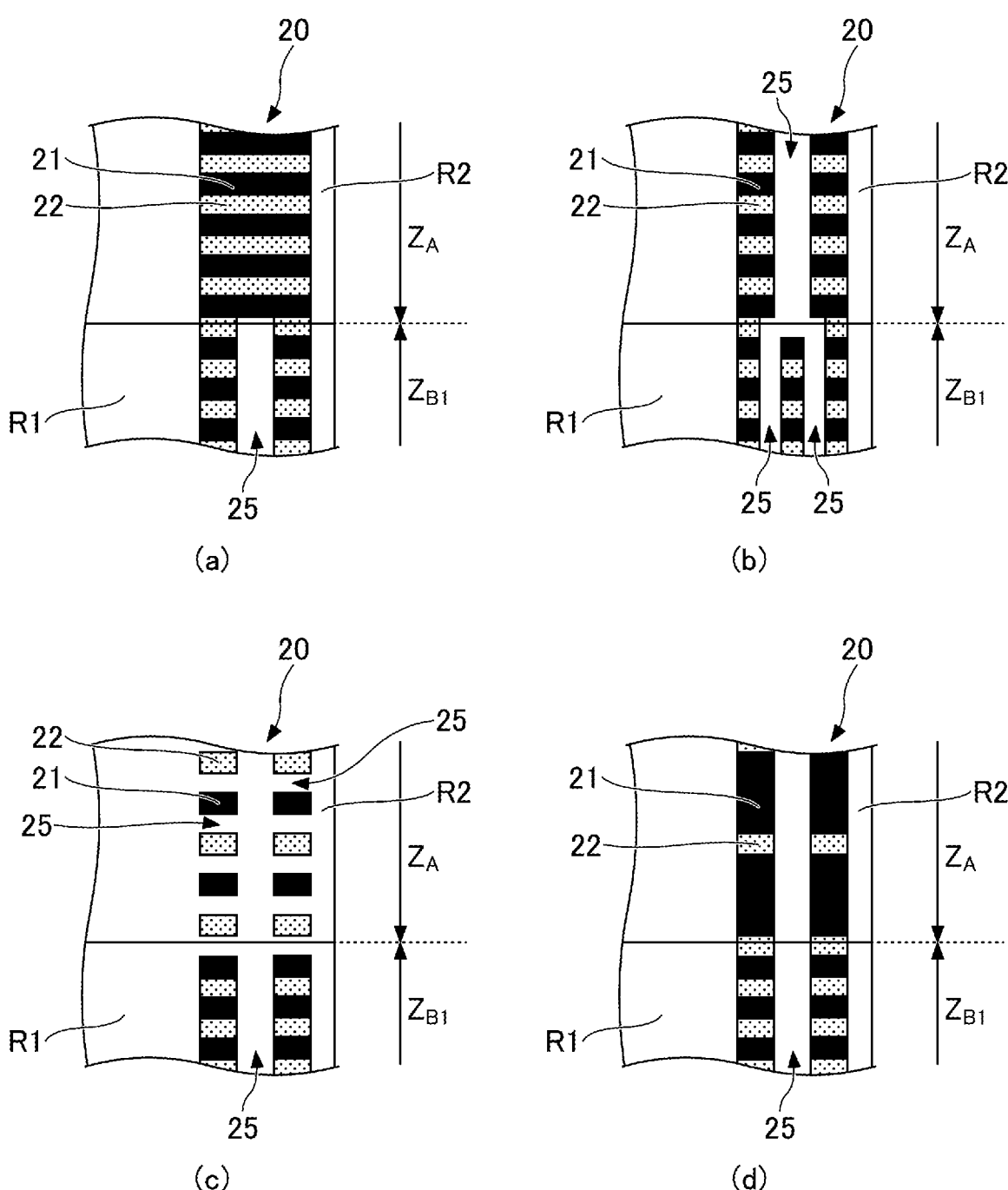
FIG. 5 is a plan view of a portion of the individually wrapped absorbent article in which a seal portion has a different configuration depending on the zone.

Further, other examples in which the strength of the seal portion 20 differs depending on the number of overlapping portions of the wrapping sheet 10 is depicted in FIG. 5. FIG. 5 is an enlarged plan view of a region located near the boundary between the second region R2 and the first region R1 (that is, a region near the opposite end 12 in the first direction D1 of the second region R2), and located at one edge portion in the second direction D2 of the individually wrapped absorbent article 100.

For example, as illustrated in FIG. 5 (*a*), a seal portion 20 is formed such that, in the first thin zone $Z_{B1}$, two seal lines are formed and a non-compressed portion 25 is formed between the seal lines, and in the thick zone $Z_A$, a non-compressed portion is not formed in the second direction D2. In this example, the force applied to form the seal portion 20 is dispersed in the second direction D2 in the thick zone $Z_A$ during a compression process when the individually wrapped absorbent article is manufactured. Therefore, the seal portion 20 can have lower seal strength in the thick zone $Z_A$ than in the first thin zone $Z_{B1}$.

In the example illustrated in FIG. 5 (*b*), in the first thin zone $Z_{B1}$, three seal lines are formed, and non-compressed portions 25 are formed between two adjacent seal lines, and in the thick zone $Z_A$, two seal lines are formed. Further, in this example, the length (width) in the second direction D2 of a compressed portion (including compressed recesses 21 and compressed projections 22) is larger in the thick zone $Z_A$ than in the thin zone $Z_{B1}$. In this example, the force applied to form a seal portion 20 is dispersed in the second direction D2 in the thick zone $Z_A$ during a compression process when the individually wrapped absorbent article is manufactured. Therefore, the seal portion 20 can have lower seal strength in the thick zone $Z_A$ than in the first thin zone $Z_{B1}$.

As illustrated in FIG. 5 (*d*), the length in the first direction D1 of a compressed portion (including compressed recesses 21 and compressed projections 22) can be larger in the thick zone $Z_A$ than in the first thin zone $Z_{B1}$. Accordingly, engagement of projections and recesses formed in the thick zone $Z_A$ of the wrapping sheet 10 is decreased. Therefore, a seal portion 20 can have lower seal strength in the thick zone $Z_A$ than in the first thin zone $Z_{B1}$.

As illustrated in FIG. 5 (*c*), the pitch in the first direction D1 of compressed recesses 21 can be larger in the thick zone $Z_A$ than in the thin zone $Z_{B1}$. Therefore, a seal portion 20 can have lower seal strength in the thick zone $Z_A$ than in the first thin zone $Z_{B1}$.

(Method for Manufacturing Individually Wrapped Absorbent Article)

Figure 6:
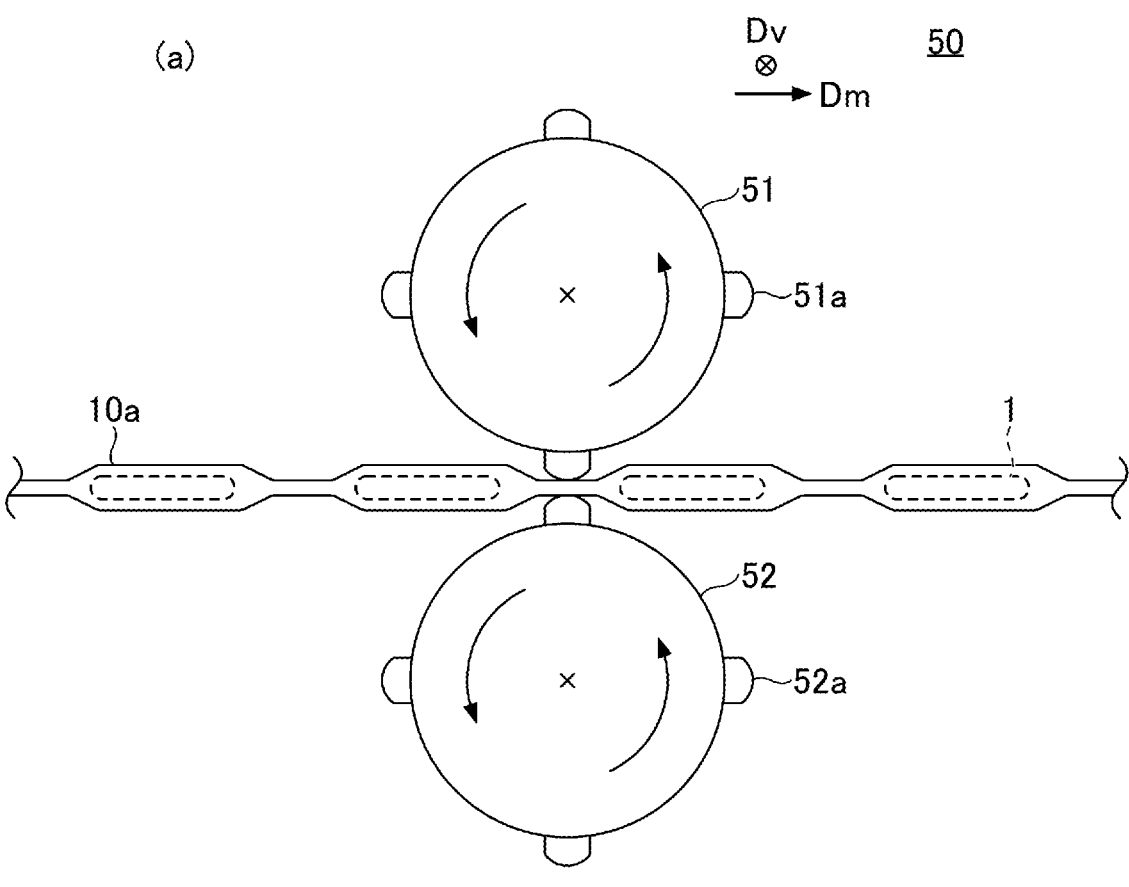
FIG. 6 is a diagram illustrating a method for manufacturing the individually wrapped absorbent article according to an embodiment.
Figure 6:
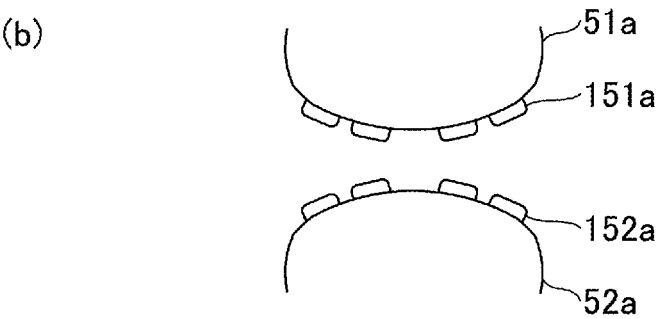

FIG. 6 (*a*) illustrates a schematic diagram illustrating a manufacturing apparatus 50 of the individually wrapped absorbent article 100 (FIG. 1 and FIG. 3) according to the embodiment. As illustrated in FIG. 6 (*a*), rolls 51 and 52 (a first roll 51 and a second roll) can be used to manufacture the individually wrapped absorbent article 100. The rolls 51 and 52 are a pair of pressing rolls facing each other. More specifically, a plurality of absorbent articles 1 are disposed spaced apart from each other on the inner surface of an elongate original wrapping sheet 10*a* that is to be conveyed in a conveying direction (machine direction) Dm. Then, the original wrapping sheet 10*a* is folded together with the absorbent articles 1 in a direction Dv that is perpendicular to the conveying direction Dm. At this time, a region including one end of the original wrapping sheet 10*a* and a region including the opposite end are folded toward the inner surface of the original wrapping sheet 10*a*. That is, the direction Dv corresponds to the first direction D1 of an ultimately obtained individually wrapped absorbent article 100. Next, the original wrapping sheet 10*a* is pressed by the pressing rolls 51 and 52. As a result, edge portions of individually wrapped absorbent articles are sealed to form seal portions 20. Note that when seal portions 20 are formed, edge portions of two adjacent individually wrapped absorbent articles, which are uncut, can be sealed at the same time. The individually wrapped absorbent articles may be cut and separated simultaneously when the seal portions 20 are formed.

The pressing roll 51 may be provided with pressing portions 51*a*, 51*a*, . . . intermittently in the circumferential direction, and the pressing roll 52 may be provided with pressing portions 52*a*, 52*a*, . . . intermittently in the circumferential direction. The pressing portions 51*a*, 51*a*, . . . are disposed facing the pressing portions 52*a*, 52*a*, . . . . The original wrapping sheet 10*a* is compressed between the pressing portions 51*a* and the pressing portions 52*a* and seal portions 20 are formed.

Further, as illustrated in FIG. 6 (*b*), teeth 151*a*, 151*a*, . . . extending in the direction Dv are formed on the surface of a pressing portion 51*a* of the pressing roll 51 and arranged in the circumferential direction. In addition, teeth 152*a*, 152*a* . . . extending in the direction Dv are formed on the surface of a pressing portion 52*a* of the pressing roll 52 and arranged in the circumferential direction. The teeth 151*a* (first teeth) of the pressing portion 51*a* are configured to face and engage with the teeth 152*a* (second tooth teeth) of the pressing portion 52*a*.

Figure 7:
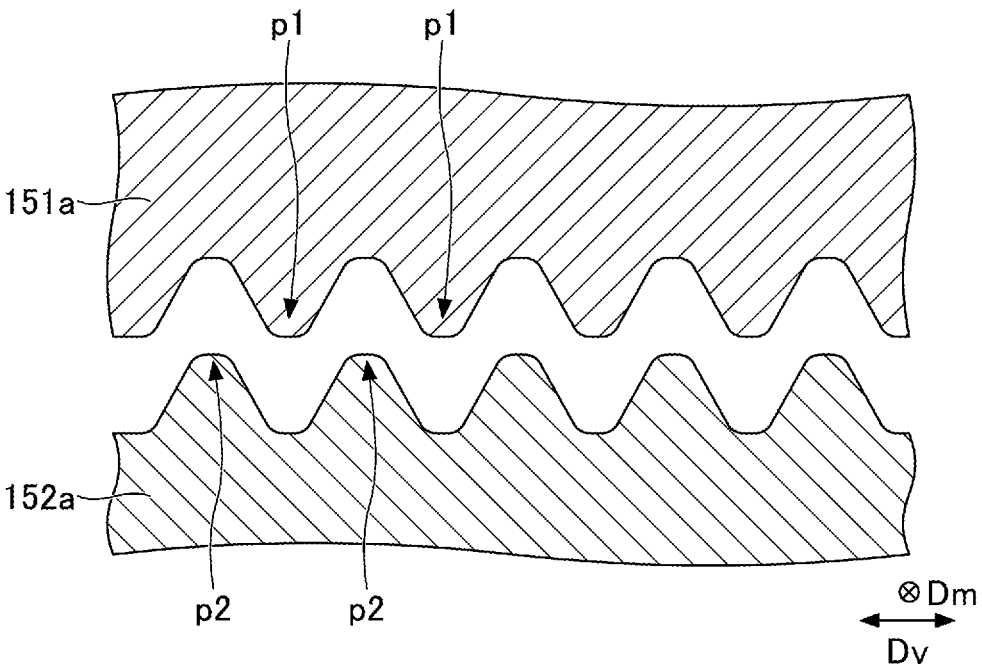
FIG. 7 is an enlarged view of teeth of a pair of pressing rolls.

FIG. 7 is a cross-sectional view of a tooth 151*a* and a tooth 152*a* taken along the direction Dv. As illustrated in FIG. 7, the tooth 151*a* and the tooth 152*a* are configured to engage with each other. That is, a projection p1 of the tooth 151*a* is configured to enter between projections p2, p2. In the example illustrated in FIG. 7, when the tooth 151*a* directly engages with the tooth 152*a*, the tooth 151*a* can engage with the tooth 152*a* with substantially no gap. Therefore, the original wrapping sheet 10*a* can be compressed along the direction Dv, and thus, compressed recesses 21 and compressed projections 22 can be continuously formed along the first direction D1 (FIG. 3). When the pressing rolls are heated to, for example, 80° C. or more, the engaging teeth 151*a* and 152*a* are thermally expanded, thus making it possible to reduce the distance between the tooth 151*a* and the tooth 152*a*. Accordingly, compression can be performed at higher pressure, and the seal strength can be increased.

Figure 8:
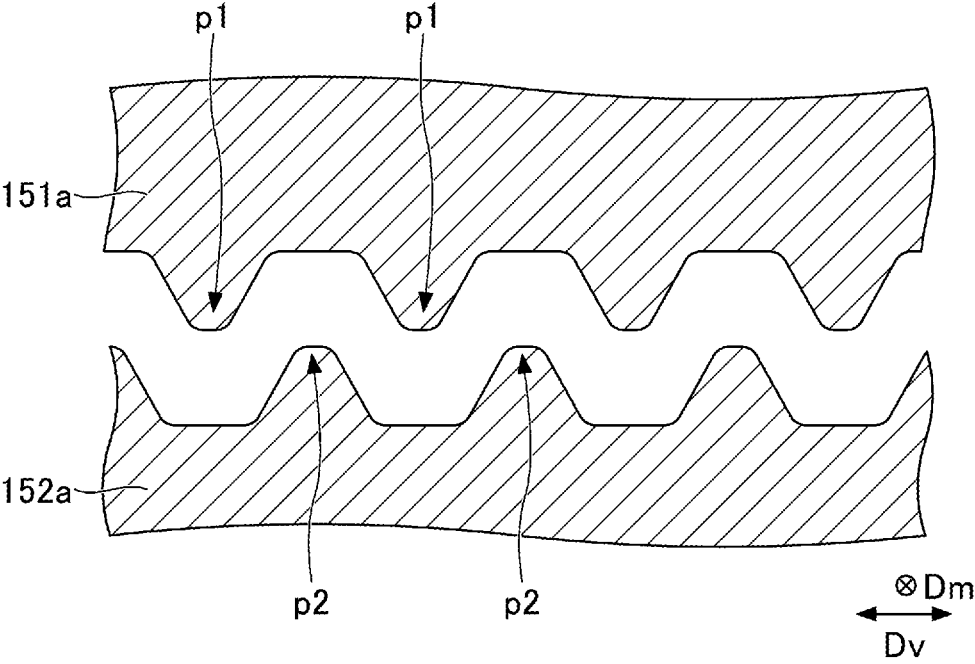
FIG. 8 is a diagram illustrating another example of teeth of a pair of pressing rolls.

FIG. 8 illustrates another example of a tooth 151*a* and a tooth 152*a*. Similar to the example illustrated in FIG. 7, in the example illustrated in FIG. 8, the tooth 151*a* and the tooth 152*a* are configured to engage with each other. However, in the example illustrated in FIG. 8, projections p1 and projections p2 are arranged at large pitches. Thus, when the tooth 151*a* directly engages with the tooth 152*a*, gaps are formed in the direction Dv. By using the tooth 151*a* and the tooth 152*a* illustrated in FIG. 8, a non-compressed portion is formed between compressed portions (each including compressed recesses 21 and compressed projections 22).

According to an embodiment of the present invention, a method for manufacturing an individually wrapped absorbent article that includes an absorbent article and a wrapping sheet configured to wrap the absorbent article is provided. The method includes disposing the absorbent article on an inner surface of the wrapping sheet; folding the wrapping sheet toward the inner surface of the wrapping sheet so as to cause a first region including one end in a first direction of the wrapping sheet and a second region including an opposite end in the first direction to overlap with each other; and pressing each edge portion in a second direction of the wrapping sheet between a pair of rolls so as to form a seal portion. The second direction is perpendicular to the first direction, and the rolls face each other. The seal portion includes a plurality of compressed recesses and compressed projections formed between the compressed recesses.

EXAMPLES

Forming Seal Portions

Example 1

A paper material having a basis weight of 30.5 g/m² and a width of 250 mm was prepared and tri-folded in the widthwise direction of the paper material as illustrated in FIG. 2. Then, seal portions, each having a length of approximately 110 mm, were formed along the folding direction (corresponding to the first direction D1 in FIG. 1) of a wrapping sheet by using a pair of pressing rolls that have engaging teeth. According to the above-described pair of pressing rolls, edge portions of two adjacent individually wrapped absorbent articles are sealed at the same time to form seal portions. Therefore, after the seal portions were formed, the paper material was cut and the individually wrapped absorbent articles were separated. As a result, a sample including a seal portion, which corresponds to a seal portion at one edge portion of one individually wrapped compressed recesses, and the width w of the compressed recess in the seal portion were as indicated in Table 1.

Example 2

A seal portion was formed in the same manner as Example 1, except that pressing rolls having different teeth were used. In the pressing rolls used in Example 2, the height of the teeth was 0.6 mm. However, an obtained pattern in a plan view was the same as the pattern illustrated in FIG. 9 (*a*) (the same as the pattern in Example 1) in a plan view. The dimensions of the seal portion were as indicated in Table 1.

Examples 3 to 7

Figure 9:
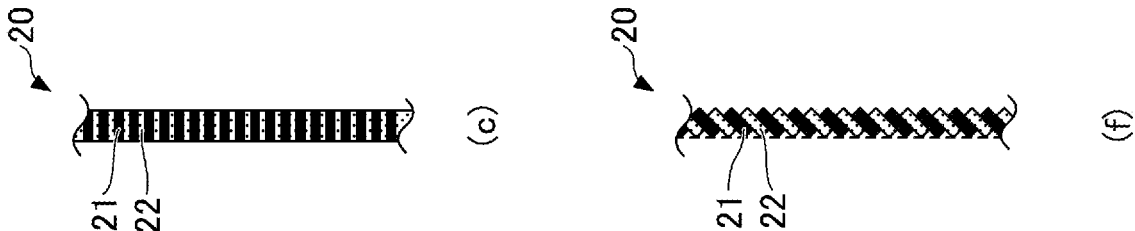
FIG. 9 is a diagram illustrating patterns of seal portions in a plan view according to examples.
Figure 9:
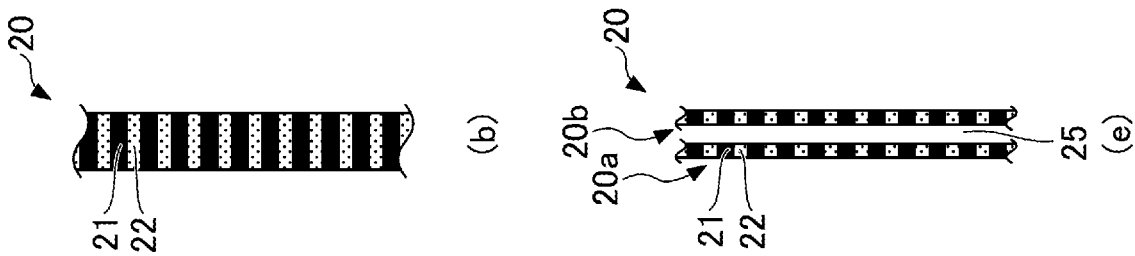
Figure 9:
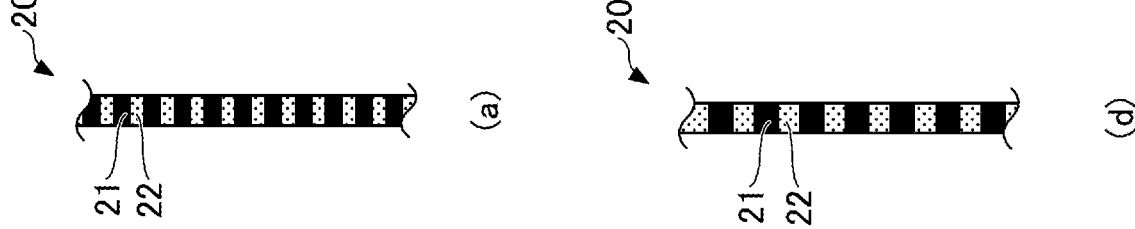

Seal portions having patterns illustrated in FIG. 9 (*b*) through FIG. 9 (*f*) in a plan view were formed in the same manner as Example 1, except that pressing rolls having different teeth were used. The dimensions of each of the seal portions were as indicated in Table 1.

<Measuring Tensile Strength (Peel Strength)>

The seal strength of each of the seal portions in Examples 1 to 7 was measured. In each sample, the end (corresponding to the opposite end 12 of the second region R2 in FIG. 1) of the last folded portion of a tri-folded sheet was peeled by 3 mm. Then, an adhesive tape having a 2.5-mm width was attached to the peeled portion, and the adhesive tape 2C was clamped in one clamp of a tensile testing machine. Further, a portion near the first folding line of the tri-folded sheet was clamped in the other clamp of the tensile testing machine. The average integrated strength was calculated at a distance between chucks of 10 mm and a speed of 100 mm/min. In order to avoid measuring breaking strength, the measurement was completed with 3 mm of each of the seal portions being left unpeeled.

TABLE 1

| | EXAMPLE 1 | EXAMPLE 2 | EXAMPLE 3 | EXAMPLE 4 | EXAMPLE 5 | EXAMPLE 6 | EXAMPLE 7[*1] |
|---|---|---|---|---|---|---|---|
| HEIGHT OF ROLL TEETH (mm) | 0.8 | 0.6 | 0.8 | 0.8 | 0.8 | 0.8 | 0.8 |
| LENGTH $L_1$ IN FIRST DIRECTION OF COMPRESSED RECESS (mm) | 1.75 | 1.75 | 1.75 | 1 | 2.5 | 1.75 | 4.07 |
| DISTANCE Δ L IN FIRST DIRECTION BETWEEN TWO ADJACENT COMPRESSED RECESSES (mm) | 1.75 | 1.75 | 1.75 | 1 | 2.5 | 1.75 | 4.07 |
| LENGTH w IN SECOND DIRECTION OF COMPRESSED RECESS (mm) | 3 | 3 | 6 | 3 | 3 | 1.75 | 2.83 |
| NUMBER OF SEAL LINES | 1 | 1 | 1 | 1 | 1 | 2 | 1 |
| TENSILE STRENGTH WHEN SECOND AREA IS OPENED (N) | 0.05 | 0.02 | 0.06 | 0.08 | 0.03 | 0.08 | 0.05 |
| TENSILE STRENGTH WHEN FIRST AREA IS OPENED (N) | 0.07 | NA[*2] | 0.06 | 0.09 | 0.04 | 0.09 | 0.06 |

[*1]The shape of a compressed recess in a plan view was a rectangular shape inclined at 45° with respect to the first direction (FIG. 9 (f)).
[*2]Impossible to measure because the first region and the third region were not bonded.

absorbent article, was obtained. Note that the line speed was 10 m/min, the upper-side roll of the pair of rolls was heated to 100° C., the lower-side roll was heated to 97° C. when pressure was applied.

In Example 1, the pressing rolls whose teeth has a height of 0.8 mm were used to form the seal portion. The seal portion had a pattern illustrated in FIG. 9 (*a*) in a plan view. The length L in the first direction D1 of a compressed recess, the distance ΔL in the first direction between two adjacent From the results of Example 1 and Example 2, it is found that as the height of teeth (height of projections of teeth) increases, the tensile strength and the seal strength increase. Further, from the results of Example 1 and Example 6, it is found that the tensile strength increases if a non-compressed portion is formed in the second direction (if a plurality of seal lines are formed). In addition, from the results of Example 1 and Example 4, it is found that the tensile strength increases as the length of a compressed recess in the first direction (the lengthwise direction of a wrapping sheet) decreases.

In the following, specific embodiments of the present invention will be appended.

APPENDIX 1

According to an embodiment described in Appendix 1, an individually wrapped absorbent article that includes an absorbent article, and a wrapping sheet configured to wrap the absorbent article is provided. The wrapping sheet is folded toward an inner surface of the wrapping sheet so as to cause a first region including one end in a first direction of the wrapping sheet and a second region including an opposite end in the first direction to overlap with each other, and a seal portion is formed at each edge portion in a second direction of the wrapping sheet. The second direction is perpendicular to the first direction. The seal portion includes a plurality of compressed recesses and compressed projections along the first direction. The compressed projections are formed between the compressed recesses.

According to the embodiment described in Appendix 1, the seal portion including the compressed recesses and the compressed projections (which may be collectively referred to as a compressed portion) is formed by densifying overlapping portions of the wrapping sheet. Therefore, when the seal portion is formed, the surface of the wrapping sheet is not necessarily required to be denatured by heating or other materials (including an adhesive and the like) are not necessarily required to be added, Thus, complicated work can be avoided when the individually wrapped absorbent article is manufactured. Further, with a structure in which the compressed projections and compressed recesses are arranged adjacent to each other, the overlapping portions of the wrapping sheet can be engaged and firmly fitted together, thereby providing high seal strength. Accordingly, the individually wrapped absorbent article can have sufficient seal strength such that the wrapping sheet can be formed of any of various materials.

APPENDIX 2

According to an embodiment described in Appendix 2, the compressed recesses and the compressed projections are formed without portions of the wrapping sheet being fused.

According to the embodiment described in Appendix 2, because portions of the wrapping sheet are not fused, there is no need to adjust a temperature for heat fusion of the portions of the wrapping sheet or there is no need to perform a heating process, thus avoiding complicated manufacturing work and also reducing manufacturing costs.

APPENDIX 3

According to an embodiment described in Appendix 3, the wrapping sheet is formed of a refractory material, or includes a layer of a refractory material on the surface of the wrapping sheet.

According to the embodiment described in Appendix 3, the wrapping sheet formed of a refractory material or including a layer of a refractory material on its surface can be utilized. In a conventional configuration in which a seal portion is formed by heat fusion, such a wrapping sheet formed of a refractory material or including a layer of a refractory material would not be utilized. Conversely, according to the present embodiment, functions or features can be added to the wrapping sheet. For example, refractory ink can be applied to the surface of the wrapping sheet, thus improving the design of the wrapping sheet.

APPENDIX 4

According to an embodiment described in Appendix 4, the wrapping sheet includes paper.

According to the embodiment described in Appendix 4, the wrapping sheet can have a natural texture. In addition, the environmental load at the time of manufacturing and/or disposal of the individually wrapped absorbent article can be reduced.

APPENDIX 5

According to an embodiment described in Appendix 5, the seal portion includes a plurality of seal lines along the first direction, and a non-compressed portion is formed between the seal lines.

According to the embodiment described in Appendix 5, a plurality of seal lines are formed. Each of the seal lines includes a plurality of compressed recesses and compressed projections formed between the compressed recesses, and a non-compressed portion is formed between the seal lines. Therefore, as compared to a single seal line that is continuously formed in the second direction, pressure can be concentrated on the seal lines disposed spaced apart from each other when the seal portion is formed at the time of manufacturing the individually wrapped absorbent article. Accordingly, compressed portions can be compressed at higher pressure, and the seal strength can be thus increased.

APPENDIX 6

According to an embodiment described in Appendix 6, a thin zone, in which the number of overlapping portions of the wrapping sheet is relatively small, and a thick zone, in which the number of overlapping portions of the wrapping sheet is relatively large, are formed. The overlapping portions are overlapped by folding the wrapping sheet. The seal portion has lower seal strength in the thick zone than in the thin zone.

According to the embodiment described in Appendix 6, the individually wrapped absorbent article has zones in which the number of overlapping portions of the wrapping sheet differs. With this configuration, in the thick zone in which the number of overlapping portions of the wrapping sheet is relatively large, compressed portions are compressed at higher pressure, and the seal strength thus tends to be increased. If the seal strength in the thick zone is excessively high, the individually wrapped absorbent article would not be smoothly opened. Conversely, if the entire seal strength is reduced, the individually wrapped absorbent article would be unintentionally opened in the thin zone. In view of the above, according to the present embodiment, the seal portion has lower seal strength in the thick zone than in the thin zone. Accordingly, the individually wrapped absorbent article capable of being smoothly opened while having sufficient seal strength can be provided.

APPENDIX 7

According to an embodiment described in Appendix 7, the seal portion has a smaller thickness in the thick zone than in the thin zone.

According to the embodiment described in Appendix 7, the seal portion has a different configuration depending on the number of overlapping portions (the thickness in a zone). More specifically, the seal portion has a small thickness in the thick zone in which the number of overlapping portions is relatively large. That is, in the thick zone, compressed recesses and compressed projections included in the seal portion have small depths and have small heights. Such a seal portion including recesses of small depths and projections of small heights are formed at relatively low pressure. Further, in the thick zone, engagement of the overlapping portions of the wrapping sheet is also decreased. Accordingly, the seal portion can have lower seal strength in the thick zone than in the thin zone.

APPENDIX 8

According to an embodiment described in Appendix 8, a method for manufacturing an individually wrapped absorbent article that includes an absorbent article and a wrapping sheet configured to wrap the absorbent article is provided. The method includes disposing the absorbent article on an inner surface of the wrapping sheet; folding the wrapping sheet toward the inner surface of the wrapping sheet so as to cause a first region including one end in a first direction of the wrapping sheet and a second region including an opposite end in the first direction to overlap with each other; and pressing each edge portion in a second direction of the wrapping sheet between a pair of rolls so as to form a seal portion The second direction is perpendicular to the first direction, and the rolls face each other. The seal portion includes a plurality of compressed recesses and compressed projections formed between the compressed recesses.

According to the embodiment described in Appendix 8, a method for manufacturing an individually wrapped absorbent article having the same effect as that of the embodiment described in Appendix 1 can be provided.

APPENDIX 9

According to an embodiment described in Appendix 9, the compressed recesses and the compressed projections are formed without portions of the wrapping sheet being fused.

According to the embodiment described in Appendix 9, a method for manufacturing an individually wrapped absorbent article having the same effect as that of the embodiment described in Appendix 2 can be provided.

APPENDIX 10

According to an embodiment described in Appendix 10, the pair of rolls includes a first roll and a second roll. The first roll includes a first tooth that has a plurality of intermittently arranged projections, and the second roll includes a second tooth that engages with the first tooth.

According to the embodiment described in Appendix 10, a method for manufacturing an individually wrapped absorbent article, having sufficient seal strength such that the wrapping sheet can be formed of any of various materials, can be provided with a relatively simple roll configuration.

This application is based on and claims priority to Japanese Patent Application No. 2020-127324, filed on Jul. 28, 2020, the entire contents of which are incorporated herein by reference.

DESCRIPTION OF THE REFERENCE NUMERALS 1 absorbent article
4 absorbent body 10 wrapping sheet
11 one end in lengthwise direction
12 opposite end in lengthwise direction
20 seal portion
20a, 20b seal lines
21 compressed recess
22 compressed projection
25 non-compressed portion
30 sealing tape
51, 52 pressing roll
51a, 52a pressing portion
151a, 152a tooth
D1 first direction of wrapping sheet
D2 second direction of wrapping sheet
F1 first folding line
F2 second folding line
p1, p2 projection of tooth
R1 first region
R2 second region
R3 third region
ZA thick zone
ZB1 first thin zone
ZB2 second thin zone

The invention claimed is:

1. An individually wrapped absorbent article comprising:
an absorbent article; and
a wrapping sheet configured to wrap the absorbent article,
wherein the wrapping sheet is folded toward an inner surface of the wrapping sheet so as to cause a first region including one end in a first direction of the wrapping sheet and a second region including an opposite end in the first direction to overlap with each other, and a seal portion is formed at each edge portion in a second direction of the wrapping sheet, the second direction being perpendicular to the first direction,
wherein the seal portion includes a plurality of compressed recesses and compressed projections along the first direction, the compressed projections being formed between the compressed recesses,
wherein a thin zone, in which the number of overlapping portions of the wrapping sheet is relatively small, and a thick zone, in which the number of overlapping portions of the wrapping sheet is relatively large, are formed, the overlapping portions being overlapped by folding the wrapping sheet, and
wherein the seal portion has lower seal strength in the thick zone than in the thin zone.

2. The individually wrapped absorbent article according to claim 1, wherein the compressed recesses and the compressed projections are formed without portions of the wrapping sheet being fused.

3. The individually wrapped absorbent article according to claim 1, wherein the wrapping sheet is formed of a refractory material, or includes a layer of a refractory material on a surface of the wrapping sheet.

4. The individually wrapped absorbent article according to claim 1, wherein the wrapping sheet includes paper.

5. The individually wrapped absorbent article according to claim 1, wherein the seal portion includes a plurality of seal lines along the first direction, and a non-compressed portion is formed between the seal lines.

6. The individually wrapped absorbent article according to claim 1, wherein the seal portion has a smaller thickness in the thick zone than in the thin zone.

7. A method for manufacturing an individually wrapped absorbent article that includes an absorbent article and a wrapping sheet configured to wrap the absorbent article, the method comprising:

disposing the absorbent article on an inner surface of the wrapping sheet;

folding the wrapping sheet toward the inner surface of the wrapping sheet so as to cause a first region including one end in a first direction of the wrapping sheet and a second region including an opposite end in the first direction to overlap with each other; and pressing each edge portion in a second direction of the wrapping sheet between a pair of rolls so as to form a seal portion, the second direction being perpendicular to the first direction, and the rolls facing each other, wherein the seal portion includes a plurality of compressed recesses and compressed projections formed between the compressed recesses, wherein the method further includes forming a thin zone, in which the number of overlapping portions of the wrapping sheet is relatively small, and a thick zone, in which the number of overlapping portions of the wrapping sheet is relatively large, the overlapping portions being overlapped by folding the wrapping sheet, and wherein the seal portion has lower seal strength in the thick zone than in the thin zone.

8. The method for manufacturing the individually wrapped absorbent article according to claim 7, wherein the compressed recesses and the compressed projections are formed without portions of the wrapping sheet being fused.

9. The method for manufacturing the individually wrapped absorbent article according to claim 7, wherein the pair of rolls includes a first roll and a second roll, the first roll including a first tooth that has a plurality of intermittently arranged projections, and the second roll including a second tooth that engages with the first tooth.

\* \* \* \* \*